(12) United States Patent
Saint-Louis-Augustin et al.

(10) Patent No.: US 11,999,682 B2
(45) Date of Patent: Jun. 4, 2024

(54) METHOD FOR PREPARING POLYTHIOLS

(71) Applicant: Arkema France, Colombes (FR)

(72) Inventors: Pascal Saint-Louis-Augustin, Billere (FR); Georges Fremy, Sauveterre de Bearn (FR); Bernard Monguillon, Bayonne (FR); Louis Corbel, Tarbes (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 16/483,298

(22) PCT Filed: Feb. 6, 2018

(86) PCT No.: PCT/FR2018/050295
§ 371 (c)(1),
(2) Date: Aug. 2, 2019

(87) PCT Pub. No.: WO2018/146415
PCT Pub. Date: Aug. 16, 2018

(65) Prior Publication Data
US 2020/0010412 A1    Jan. 9, 2020

(30) Foreign Application Priority Data
Feb. 13, 2017 (FR) ........................... 1751160

(51) Int. Cl.
*C07C 319/04* (2006.01)

(52) U.S. Cl.
CPC ................. *C07C 319/04* (2013.01)

(58) Field of Classification Search
CPC ................................. C07C 319/04
See application file for complete search history.

(56) References Cited

U.S. PATENT DOCUMENTS

| | | | | |
|---|---|---|---|---|
| 2,531,602 A | * | 11/1950 | Bell | C07C 319/18 568/59 |
| 2,865,965 A | | 12/1958 | May et al. | |
| 3,069,472 A | * | 12/1962 | Loev | C07C 1/322 568/69 |
| 3,397,243 A | * | 8/1968 | Kite | C07C 319/16 568/59 |
| 3,803,260 A | * | 4/1974 | Porchey et al. | C07C 11/02 585/654 |
| 4,233,128 A | | 11/1980 | Ollivier et al. | |
| 4,443,310 A | | 4/1984 | Arretz et al. | |
| 4,565,893 A | | 1/1986 | Arretz et al. | |
| 4,943,662 A | * | 7/1990 | Arretz | C07C 319/06 568/66 |
| 7,339,083 B2 | | 3/2008 | Fremy et al. | |
| 9,505,011 B1 | | 11/2016 | Byers et al. | |
| 2012/0035291 A1 | * | 2/2012 | Matson | C07C 321/06 522/76 |
| 2014/0235807 A1 | * | 8/2014 | Cazaux | C08F 220/14 526/214 |

FOREIGN PATENT DOCUMENTS

| | | |
|---|---|---|
| CN | 103003235 A | 3/2013 |
| EP | 1181325 B1 | 8/2006 |
| FR | 2501679 A1 | 9/1982 |
| FR | 2531426 A1 | 2/1984 |
| FR | 2844794 A1 | 3/2004 |
| GB | 1284176 | 8/1972 |
| JP | 505167 B1 | 2/1975 |
| WO | 2012018757 A1 | 2/2012 |

OTHER PUBLICATIONS

International Search Report and Written Opinion for International Application No. PCT/FR2018/050295, dated May 8, 2018—8 pages.

* cited by examiner

*Primary Examiner* — Rosalynd A Keys
(74) *Attorney, Agent, or Firm* — Buchanan Ingersoll & Rooney, PC

(57) ABSTRACT

Provided is a process for preparing polythiols by preparing a sulfhydration reaction medium, simultaneously carrying out radical sulfhydration reaction of at least one polyene and acid-catalyzed sulfhydration reaction of the polyene and recovering a mixture including at least two polythiols. Also provided is a mixture of polythiols obtained from the process described herein.

10 Claims, No Drawings

METHOD FOR PREPARING POLYTHIOLS

CROSS-REFERENCE TO RELATED APPLICATIONS

This is the national phase of International Application No. PCT/FR2018/050295, filed 6 Feb. 2018, which claims priority to French Application No. 1751160, filed 13 Feb. 2017. The disclosure of each of these applications is incorporated herein by reference in its entirety for all purposes.

FIELD OF THE INVENTION

The invention relates to the preparation of polythiols, and more particularly to a process for preparing polythiols with a controlled content of primary, secondary and tertiary thiols.

BACKGROUND OF THE INVENTION

There are various processes for obtaining polythiols depending on whether it is desired to prepare primary, secondary or tertiary polythiols.

Among the processes for preparing polythiols, the radical preparation of polythiols is known. This process predominantly leads to the production of primary polythiols, and more generally to the addition of an —SH group to the $sp^2$ carbon atoms that are the least substituted and/or that lead to the formation of the most stable radical. A process is for example disclosed in application US 2012/0035291 for preparing a polythiol composition comprising primary thiols, from a hydrocarbon compound having at least two double bonds, a phosphite compound and hydrogen sulfide.

Also known is the preparation of polythiols by acid catalysis; said catalysis allowing the formation of polythiols comprising predominantly secondary and/or tertiary thiols, and more generally the addition of an —SH group on the $sp^2$ carbon atoms that are the most substituted and/or that lead to the formation of the most stable carbocation. Thus, applications FR2844794 and FR2531426 describe a process for the acid-catalyzed manufacture of a thiol, from an olefin and hydrogen sulfide.

However, not all of these techniques make it possible to obtain polythiols with a high thiol content and with a controlled regioselectivity of the thiol groups.

Therefore there remains a need for a process for obtaining polythiols with a controlled content of primary, secondary and tertiary thiols.

SUMMARY OF THE INVENTION

The applicant discovered that it was possible to achieve this objective by means of the process which is described in the following description.

According to a first aspect, the present invention relates to a process for preparing polythiols comprising at least the steps of:
a/ preparing a sulfhydration reaction medium comprising the bringing into contact of:
  at least one polyene;
  at least one radical initiator;
  at least one acid catalyst;
  at least one sulfhydryl group donor compound;
  optionally, at least one solvent;
b/ simultaneously carrying out the radical sulfhydration reaction of said at least one polyene and the acid-catalyzed sulfhydration reaction of said at least one polyene;

c/ recovering a mixture comprising at least two polythiols.

The process according to the invention makes it possible to obtain a mixture comprising at least two polythiols, the at least two polythiols obtained generally being polythiols of the same molecular weight, but the thiol functions of which are borne by different carbon atoms. For the purposes of the present invention, the process thus makes it possible to obtain a mixture of positional isomers of polythiols. Advantageously, and very particularly preferably, the process of the invention leads to the formation of polythiols no longer containing double bonds, that is to say that all the double bonds of the starting polyene are sulfhydrated with the process according to the invention.

DETAILED DESCRIPTION OF THE INVENTION

A "polythiol" is understood to mean a compound having at least two thiol (—SH) functions.

The term "controlled" is understood to mean the production of polythiols with a regioselectivity of thiol functions which is different from that which would have been obtained by carrying out a radical sulfhydration reaction alone or else an acid-catalyzed sulfhydration reaction alone.

Indeed, when the radical sulfhydration reaction is carried out alone, the least substituted polythiol is predominantly obtained, i.e. the majority of the thiol functions are attached to the carbon atoms that are the least substituted and/or derived from the formation of the most stable radicals.

As regards the acid-catalyzed sulfhydration reaction, when the latter is carried out alone, the most substituted polythiol is predominantly obtained, i.e. the majority of the thiol functions are attached to the carbon atoms that are the most substituted and/or derived from the formation of the most stable carbocations.

The process according to the invention, by allowing the simultaneous execution of the two abovementioned reactions makes it possible to control, i.e. to modify or even to reverse this regioselectivity. Indeed, the polythiols obtained in the minority after a radical sulfhydration reaction alone or after an acid-catalyzed sulfhydration reaction alone become the polythiols predominantly obtained by the process according to the invention.

A "polyene" is understood to mean a compound with a hydrocarbon chain that comprises at least two unsaturations in double bond form ("olefinic" unsaturation). This hydrocarbon chain may be linear or cyclic, saturated or unsaturated, may optionally comprise one or more heteroatoms, and may be interrupted or substituted by one or more aromatic groups. The polyene within the meaning of the present invention usually has a molar mass of between 40 g·mol$^{-1}$ and 1500 g·mol$^{-1}$, preferably between 40 g·mol$^{-1}$ and 1000 g·mol$^{-1}$ more preferably between 40 g·mol$^{-1}$ and 500 g·mol$^{-1}$ limits included.

According to one embodiment of the invention, the polyene is a hydrocarbon compound comprising from 2 to 20 double bonds, preferably from 2 to 16 double bonds, more preferably from 2 to 10 double bonds, in particular from 2 to 8 double bonds, and typically from 2 to 4 double bonds, limits included.

According to one very particularly preferred embodiment of the invention, the polyene is a hydrocarbon compound comprising 2 double bonds, preferably 3 double bonds, and more particularly 4 double bonds.

Preferably, the double bonds of the polyene are not included in a ring. More preferably, at least 2 double bonds of the polyene are not delocalized to form an aromatic ring.

According to one embodiment of the invention, the polyene comprises one or more heteroatoms chosen from columns 15, 16 and 17 of the Periodic Table of the Elements, and more particularly those chosen from sulfur, nitrogen, oxygen and phosphorus.

According to a preferred embodiment, the polyene is chosen from terpenes and derivatives thereof, comprising at least two double bonds, such as for example isoprene, limonene, myrcene, phellandrene, terpinene, ocimene, terpinolene, geraniol, citral, retinol, β-carotene, farnesene, selinene, cadinene, farnesol, humulene, linalool and nerolidol.

According to another preferred embodiment, the polyene is a compound comprising one or more heteroatoms, such as, for example, triallyl isocyanurate and its derivatives.

The radical initiator according to the invention may be any radical initiator known to those skilled in the art. The radical initiator may be chosen from a thermal initiator, such as for example heating, a photochemical initiator such as for example radiation, and more particularly ultraviolet radiation, and a radical-generating organic or mineral compound, or the like, and also combinations of two or more thereof. In the case where said radical initiator is an organic or inorganic compound, it may be a peroxide such as, for example, hydrogen peroxide, sodium peroxide, potassium peroxide, tert-alkyl hydroperoxides, tert-alkyl peroxides, tert-alkyl peresters, cumene hydroperoxide, or else the radical initiator may also be azobisisobutyronitrile, 2,2-dimethoxy-1,2-diphenylethan-1-one, said radical initiators may be taken alone or as a combination of two or more thereof. It is also possible to use alkyl phosphites or else xanthene derivatives such as those described in patent application FR2501679.

According to a preferred embodiment of the invention, the radical initiation is obtained by heating and/or by radiation of light, for example of ultraviolet light.

According to another preferred embodiment of the invention, the radical initiator comprises 2,2-dimethoxy-1,2-diphenylethan-1-one, for example sold under the name Irgacure® 651, optionally as a mixture with other radical initiators as described for example in applications U.S. Pat. Nos. 4,443,310 A and 4,233,128 A.

When necessary or desired, the reaction medium may be heated at temperatures between 25° C. and 150° C., preferably between 25° C. and 100° C., in particular between 25° C. and 70° C.

When the initiation comprises an irradiation of the reaction medium, this can be carried out for example by direct or indirect photolysis, preferably direct photolysis, in a range of wavelengths extending from around 180 nm to 600 nm, preferably by ultraviolet radiation and for example having wavelengths of between 180 nm and 400 nm.

The acid catalyst is chosen from all acid catalysts known to those skilled in the art for conducting homogeneous or heterogeneous acid catalyses, and may for example be chosen from Lewis acids, acid resins such as sulfonated resins (for example a styrene-divinylbenzene copolymer as described in application FR 2531426), and catalytic compositions comprising at least one metal salt, in which the metal is chosen from metals belonging to groups 8, 9 and 10 of the Periodic Table of the Elements (as described for example in application FR 2844794), taken alone or as a combination of two or more thereof.

According to one embodiment of the invention, the acid catalyst is a sulfonated resin of styrene-divinylbenzene copolymer type, for example the Amberlyst® 15 resin.

The sulfhydryl group donor compound may be of any type known to those skilled in the art capable of generating a sulfhydryl (—SH) group under the reaction conditions, that is to say the addition of an —SH group and of a hydrogen atom to the $sp^2$ carbons of the polyene. Said sulfhydryl group donor compound may be chosen from hydrogen sulfide, thiocarboxylic acids such as, for example, thioacetic acid, and also the precursors of these compounds, taken alone or as a combination of two or more thereof. Among the precursors of the sulfhydryl group donor compounds, mention may be made, for example, of dialkyl di- and poly-sulfides, such as, for example, dimethyl disulfide (DMDS), diethyl disulfide (DEDS), dipropyl disulfide (DPDS), dibutyl disulfide (DBDS), and also higher homologs, and also the mixtures thereof in all proportions, as can be found in DSOs (or "DiSulfide Oils").

According to a preferred embodiment, the process according to the invention is carried out in the absence of solvent.

According to another preferred embodiment, the process according to the invention is carried out in the presence of solvent. The amount of solvent used may vary widely and will be easily assessed and adjusted by those skilled in the art depending on the reagents used, the reaction temperature and other reaction parameters.

When a solvent is used, this solvent may be of any type well known to those skilled in the art and in particular a solvent chosen from water and organic compounds and mixtures thereof in all proportions. The organic compounds that can be used as solvent are typically chosen from aliphatic hydrocarbon compounds, aromatic hydrocarbon compounds optionally comprising one or more heteroatoms chosen from oxygen, sulfur, nitrogen and halogens.

The solvent can thus be chosen from hydrocarbons, ketones, alcohols, ethers, esters, sulfoxides (e.g. dimethyl sulfoxide), sulfolanes, nitriles (e.g. acetonitrile), taken alone or as a combination of two or more thereof.

According to one embodiment of the invention, the solvent is an aliphatic hydrocarbon compound in which the hydrocarbon chain is linear or cyclic, branched or unbranched, and comprises between 3 and 20 carbon atoms, preferably between 4 and 15 carbon atoms. in particular between 5 and 10 carbon atoms.

According to another embodiment of the invention, the solvent is an aromatic hydrocarbon compound comprising from 6 to 30 carbon atoms, preferably from 6 to 20 carbon atoms, in particular from 6 to 10 carbon atoms. The aromatic hydrocarbon compound may for example be chosen from benzene, toluene, xylene (ortho-xylene, para-xylene, meta-xylene) and ethylbenzene, taken alone or as a combination of two or more thereof.

According to one embodiment of the invention, the solvent is a ketone comprising from 2 to 20 carbon atoms, preferably from 2 to 10 carbon atoms, in particular from 2 to 6 carbon atoms. The ketone may thus be chosen from acetone, ethyl methyl ketone and methyl isobutyl ketone, taken alone or as a combination of two or more thereof.

According to one embodiment of the invention, the solvent is an alcohol comprising from 2 to 20 carbon atoms, preferably from 2 to 10 carbon atoms. The alcohol is chosen from methanol, ethanol, propanol, butanol, pentanol, hexanol, heptanol, octanol, benzyl alcohol, phenol, cyclohexanol, taken alone or as a combination of two or more thereof.

According to one embodiment of the invention, the solvent is an ether comprising from 2 to 20 carbon atoms, preferably from 2 to 10 carbon atoms. The ether may optionally be cyclic and may be chosen from dimethyl ether, diethyl ether, methyl ethyl ether, glycol monoethers, glycol diethers, furan, dihydrofuran, tetrahydrofuran, pyran, dihydropyran, tetrahydropyran, 1,2-dioxane, 1,3-dioxane, 1,4-dioxane.

The various elements of the reaction medium may be brought into contact by any technique known to those skilled in the art, for example by simple mixing of the starting reagents and reactants, optionally in the presence of solvent (s), it being possible for the reaction medium to be homogeneous or heterogeneous. As a variant, it is possible firstly to dissolve said at least one polyene in said at least one solvent, then to add said at least one sulfhydryl group donor compound, and to use said at least one radical initiator and said at least one acid catalyst.

The reaction is generally carried out at atmospheric pressure, but may also be carried out under negative pressure, under vacuum or under pressure, it being possible for said pressure to range from atmospheric pressure to 10 MPa (100 bar), preferably from atmospheric pressure to 5 MPa (50 bar). bars), in particular from atmospheric pressure at 2 MPa (20 bar).

The process according to the invention may be carried out at any temperature, preferably at a temperature between 25° C. and 150° C., more preferably between 25° C. and 100° C., in particular between 25° C. and 70° C., the temperature can be easily adapted depending on the nature of the reagents, solvents and types of catalysts used, and also the pressure applied to the reaction medium.

The reaction may take place between a few minutes and a few hours, the duration being dependent on the operating conditions described above.

The process of the invention is characterized in that step b/of carrying out the reaction comprises both an acid-catalyzed sulfhydration reaction of the at least one polyene and a radical sulfhydration reaction of said at least one polyene, said acid-catalyzed sulfhydration and radical sulfhydration reactions being carried out simultaneously.

The term "simultaneous" is understood to mean that the acid-catalyzed sulfhydration and radical sulfhydration reactions are carried out simultaneously and/or alternately and/or sequentially without isolation of the reaction intermediates, until the conversion, preferably until the complete conversion, of said at least one polyene to polythiols.

As indicated above, the polyene comprises at least two unsaturations in double bond form so that these two reactions can take place simultaneously on the same polyene compound. Indeed, in the example where the polyene comprises two double bonds bearing substituents that are different with respect to one another, one of them undergoes the radical sulfhydration reaction while the other undergoes the acid-catalyzed sulfhydration reaction.

When said at least one polyene comprises two double bonds bearing identical substituents (for example in the case of symmetric polyenes), it is also possible to perform, by acting on the operating conditions, both a radical sulfhydration reaction and an acid-catalyzed sulfhydration reaction, one on at least one olefinic unsaturation and the other on at least one other olefinic unsaturation.

The process according to the invention can be carried out continuously or batchwise. When the reaction takes place continuously, step b/comprises, advantageously but most often, a step of recirculating the reaction medium in a reaction loop.

It has been discovered by the applicant that the simultaneous performance of the radical sulfhydration reaction and of the acid-catalyzed sulfhydration reaction according to the process according to the invention may lead, surprisingly, to a complete conversion of said at least one starting polyene, which conversion is generally not complete when carrying out these reactions separately. Complete conversion is understood to mean a degree of conversion of greater than 90%, more generally of greater than 95%, typically of greater than 99%, and more specifically equal to 100% of the number of double bonds present in said at least one starting polyene.

The process of the invention also makes it possible to prepare polythiols with high contents of thiol functional groups and a limited or even zero content of double bonds. For example, in the case where the starting polyene has 3 double bonds and in the case of a complete conversion of said polyene, said polyene will be converted into a mixture of polythiols, each polythiol having 3 sulfhydryl (—SH) functions.

The fact of combining the radical route and the acid-catalyzed route makes it possible not only to obtain polythiols comprising primary thiols and secondary and/or tertiary thiols, but the polythiols obtained are different from those which would have been obtained if the two reactions had been carried out separately. This control of the thiol content makes it possible to adjust the reactivity of the polythiol compound formed, especially during the use thereof.

Furthermore, the process according to the invention makes it possible to increase the reaction kinetics thus leading to minimizing the formation of secondary reactions such as intramolecular reactions, and limiting the content of impurities such as sulfides.

Moreover, it has been observed that the regioselectivity of the sulfhydration reactions can be controlled by the operating conditions in the process of the present invention. Furthermore, the adjustment of the operating conditions also makes it possible to control the ratio of the polythiol isomers formed.

The mixture of polythiols obtained is isolated from the reaction medium by any method known to those skilled in the art, for example by evaporation or distillation of the solvent at atmospheric pressure or under reduced pressure. The mixture of polythiols can be purified by conventional methods also well known to those skilled in the art and for example chosen from ion exchange resin purification, filtration over activated carbon, diatomaceous earths or zeolites, and the like.

The mixture of polythiols obtained according to the process according to the invention can be used as is or else the polythiols of said mixture can be isolated by any separation method well known to those skilled in the art such as, for example, distillation, crystallization, preparative chromatography, and the like.

The present invention also relates to the mixture of at least two polythiols capable of being obtained according to the process as described above.

Thus, the mixtures of polythiols capable of being obtained according to the process of the present invention can find many applications that are quite advantageous in many fields, for example and nonlimitingly, as:
- crosslinking or vulcanizing agent;
- reagent for the preparation of sulfur compounds such as thiourethanes, polysulfides and the like;
- chain transfer agent;
- metal complexing agent;
- ore flotation agent;
- antioxidant;
- heat stabilizer;
- and the like.

The present application also relates to the use of the polythiols obtained by the process according to the invention, for example as crosslinking agents in the preparation of adhesives, glues, sealants, and coatings of the type of epoxy resins, acrylates, isocyanates and the like.

The polythiols obtained by the process according to the invention can also be used as reagents in thiol-ene reactions. Indeed, the presence of sulfhydryl groups with variable reactivity makes it possible to adjust the kinetics of the addition reaction of the thiol function to a diene group.

The polythiols obtained by the process according to the invention can also be used for the preparation of thiourethanes. Indeed, by reacting polythiols with a controlled content of thiol functions, thiourethane compounds are obtained that have a chemical structure and performance different from those that would have been obtained from conventional polythiols synthesized either by the radical route or by the acid-catalyzed route.

The polythiols obtained by the process according to the invention can also be used as precursors for the synthesis of polysulfides. Indeed, by oxidation with sulfur it is possible to obtain polysulfide compounds which can be used as additives for lubricants or for rubber. With the polythiols obtained by the process according to the invention, because of the difference in steric hindrance at the sulfur bonds, the polysulfides formed offer variable reactivities.

The polythiols obtained by the process according to the invention can act as chain transfer agents during the synthesis of polymers from monomers such as, for example, vinyl monomers, conjugated diene monomers, acrylic monomers, methacrylic monomers, and mixtures of two or more thereof in all proportions. The difference in reactivity depending on the type and content of sulfhydryl group allows improved control of the polymerization reaction.

As another use, the polythiols obtained by the process of the present invention can also be used as crosslinking agents for natural, artificial or synthetic rubbers, metal complexing agents, ore flotation agents, as oxygen sensors, as corrosion inhibitors and the like.

The present invention is now illustrated by the following example, without however imparting a limiting nature to the invention, the scope of which is determined by the following claims.

EXAMPLE

One embodiment of the process of the invention is illustrated by this example in which a photoinitiator and a radiation source are used in a photochemical reactor, said photochemical reactor comprising a recirculation loop on which a tubular reactor is installed. Filters positioned upstream and downstream of the tubular reactor prevent entrainment of the heterogeneous catalyst.

The reactor also has a heating system for heating to the desired temperature. A cooling system located after the tubular reactor on the recirculation loop makes it possible to cool or heat the liquid feed of the photochemical reactor. A pump placed on this recirculation loop makes it possible to vary the liquid flowrate.

100 g (0.73 mol) of β-myrcene (from DRT) dissolved in 1000 g of tetrahydrofuran (Aldrich) and 0.25 g of Irgacure® 651 (Ciba Specialty Chemicals) are introduced. 5 g of dry Amberlyst® 15 cation exchange resin (Aldrich) are introduced into the tubular reactor.

Under recirculation (20 l·h$^{-1}$), the reaction medium is then subjected to nitrogen bubbling in order to remove traces of residual oxygen. Added next to the reaction medium are 30 molar equivalents of hydrogen sulfide ($H_2S$). The tubular reactor is then brought to the desired temperature (100° C.). Once this temperature is reached, the lamp is then lit. The reaction medium is subjected to UV radiation (wavelength: 355-365 nm, power: 8 watts), for 6 hours at a temperature of 100° C., and a constant pressure of 1.5 MPa, adjusted by the addition of hydrogen sulfide.

The conversion is monitored by analyzing the samples by high-performance (or high-pressure) liquid chromatography.

After 6 hours the conversion of the starting polyene reached 100%. The lamp is switched off and the heating of the tubular reactor is stopped. The excess hydrogen sulfide is then purged to a thermal oxidizer by decompression of the medium, and then by stripping with nitrogen. The mixture is then evaporated under vacuum in order to remove the solvent and then distilled in order to remove the possible impurities, for example of the sulfide type.

The distilled mixture thus obtained has a purity of greater than 98% expressed by weight of trithiols formed. This distilled mixture is characterized by NMR and is found to be composed of polythiols of the following chemical structures:

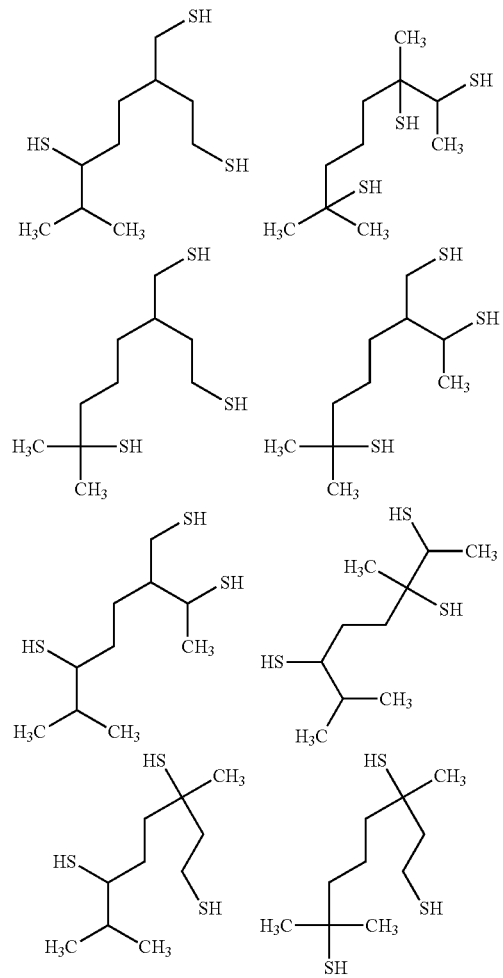

The invention claimed is:
1. A process for controlling regioselectivity of prepared polythiols comprising:
preparing a sulfhydration reaction medium comprising bringing into contact in a reactor:
at least one polyene;

at least one radical initiator that includes a photochemical radical initiator;
at least one heterogeneous acid catalyst that is a resin;
at least one sulfhydryl group donor compound;
optionally, at least one solvent;
simultaneously carrying out the radical sulfhydration reaction of said at least one polyene and the acid-catalyzed sulfhydration reaction of said at least one polyene which includes irradiation of the reaction medium at wavelengths sufficient to obtain radical initiation; and
recovering a mixture comprising least substituted polythiols and most substituted polythiols, wherein for the least substituted polythiols, the sulfhydryl group of the sulfhydryl group donor is predominantly attached to the least substituted carbon atoms of the polythiol when the sulfhydration reaction is radical initiated, and wherein for the most substituted polythiol, the sulfhydryl group of the sulfhydryl group donor is predominantly attached to the most substituted carbon atoms of the polythiol when the sulfhydration reaction is acid-catalyzed, and where the ratio between the least substituted polythiol formed and the most substituted polythiol formed is controlled by adjusting the radical initiated and the acid-catalyzed reaction conditions,
wherein said at least one sulfhydryl group donor compound is chosen from hydrogen sulfide, thiocarboxylic acids and dialkyl di- and poly-sulfides, taken alone or as a combination of two or more thereof.

2. The process according to claim 1, wherein said at least one polyene is a compound with a hydrocarbon chain that comprises at least two unsaturations in double bond form, it being possible for said chain to be linear or cyclic, saturated or unsaturated, and to optionally comprise one or more heteroatoms chosen from columns 15, 16 and 17 of the Periodic Table of the Elements, and to be interrupted or substituted by one or more aromatic groups.

3. The process according to claim 1, wherein said at least one polyene is a hydrocarbon compound comprising from 2 to 20 double bonds, limits included.

4. The process according to claim 1, wherein said at least one polyene is chosen from triallyisocyanurate and derivatives thereof, terpenes and derivatives thereof, comprising at least two double bonds.

5. The process according to claim 1, wherein said at least one radical initiator also includes a thermal initiator.

6. The process according to claim 5, wherein said at least one radical initiator is chosen from peroxides, hydroperoxides, azobisisobutyronitrile, 2,2-dimethoxy-1,2-diphenylethan-1-one, alkyl phosphites and xanthene derivatives, taken alone or as a combination of two or more thereof.

7. The process according to claim 1, carried out in the absence of solvent.

8. The process according to claim 1, wherein said at least one sulfhydryl group donor compound is a disulfide oil.

9. The process according to claim 1, wherein the irradiation is ultraviolet radiation.

10. The process according to claim 9, wherein the ultraviolet radiation has a wavelength of between 180 nm and 400 nm.

* * * * *

UNITED STATES PATENT AND TRADEMARK OFFICE
CERTIFICATE OF CORRECTION

Page 1 of 1

PATENT NO. : 11,999,682 B2
APPLICATION NO. : 16/483298
DATED : June 4, 2024
INVENTOR(S) : Pascal Saint-Louis-Augustin et al.

It is certified that error appears in the above-identified patent and that said Letters Patent is hereby corrected as shown below:

In the Claims

In Column 9, Claim 1, Line 14: replace "sulhydryl" with -- sulfhydryl --.

In Column 9, Claim 1, Line 18: replace "sulhydryl" with -- sulfhydryl --.

In Column 10, Claim 4, Line 11: replace "triallyisocyanurate" with -- triallyl isocyanurate --.

Signed and Sealed this
Eighth Day of April, 2025

Coke Morgan Stewart
*Acting Director of the United States Patent and Trademark Office*